United States Patent [19]

Garzia

[11] 4,115,570
[45] Sep. 19, 1978

[54] MORPHOLINE COMPOUNDS AND METHODS OF USE

[75] Inventor: Aldo Garzia, Lodi (Milan), Italy

[73] Assignee: Istituto Chemioterapico Italiano, S.p.A., Italy

[21] Appl. No.: 554,177

[22] Filed: Feb. 28, 1975

[51] Int. Cl.$^2$ .................. A61K 31/535; C07D 295/18
[52] U.S. Cl. .................. 424/248.57; 424/248.58; 424/250; 424/267; 424/324; 260/293.76; 260/558 R; 260/559 R; 544/174; 544/176; 544/391
[58] Field of Search .................. 260/558, 559, 247.7, 260/268, 293.86, 247.7 V; 424/248, 267, 250, 324, 248.57, 248.58; 544/174

[56] References Cited

U.S. PATENT DOCUMENTS

2,851,494  9/1958  Ehrhart et al. .............. 260/247.2 A

FOREIGN PATENT DOCUMENTS

7,016,097  5/1971  Netherlands .................. 260/268 C
92,139  5/1958  Norway .................. 260/247.7

OTHER PUBLICATIONS

Chiron et al., I, Bull. Chim. Soc. Fr., pp. 575–583 (1970).
Chiron et al., II, Bull. Chim. Soc. Fr., pp. 2145–2153 (1971).
Wawzonek et al., J. Org. Chem., vol. 36, p. 2470 (1971).
Vereshchagin et al., J. Org. Chem. USSR, vol. 9, pp. 514–518 (1973).
Woodman et al., J. Org. Chem., vol. 38, pp. 4288–4295 (1973).
Ramachandran et al., Chem. Abst., vol. 77, item 19329 (1972).
Sucrow et al., Ber., vol. 105, pp. 1621–1633 (1972).
Isowa et al., Chem. Abst., vol. 70, item 114858 (1969).
Seefelder, Chem. Abst., vol. 56, col. 1326 (1962).
Padwa et al., J. Am. Chem. Soc., vol. 93, pp. 2928–2935 (1971).
Laurence et al., Chem. Abst., vol. 70, item 77089 (1969).
Bersch et al., Chem. Abst., vol. 52, col. 14628 (1958).
Cromwell et al., J. Am. Chem. Soc., vol. 80, pp. 4573–4577 (1958).
Lukes et al., Chem. Abst., vol. 53, col. 15075 (1959).
Garzia et al., "Riv. di Farm.", VI, 75–78 (1975).
Tammiso, "Riv. di Farm.", VI, 71–74 (1975).
Sandrini et al., "Riv. di Farm.", VI; 7–15, 17–22, 23–33, 351–355 (1975).

Primary Examiner—Natalie Trousof
Assistant Examiner—R. W. Ramsuer
Attorney, Agent, or Firm—Bernard & Brown

[57] ABSTRACT

Compounds of the formula

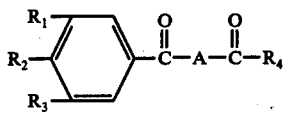

wherein A is alkylene, $R_1$, $R_2$, and $R_3$ are hydrogen or lower alkoxy, and $R_4$ is

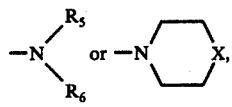

in which $R_5$ and $R_6$ are hydrogen or lower alkyl, with the proviso that at least one of $R_5$ and $R_6$ is lower alkyl, and $>X$ is oxygen,

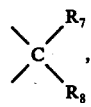

or $>N-R_7$ wherein $R_7$ and $R_8$ are hydrogen or lower alkyl, depress the activity of the central nervous system when administered to a living animal.

13 Claims, No Drawings

MORPHOLINE COMPOUNDS AND METHODS OF USE

This invention relates to novel compounds, processes for their preparation, and methods of their use for depressing the activity of the central nervous system of a living body. More particularly, this invention is directed to amide esters of benzoyl alkanoic acids.

Many agents which have depressant effects on the central nervous system of living animals are known. These agents have been used, for instance, as anticonvulsants, sedatives, tranquilizers, and the like. For example, one such central nervous system depressant is chlorpromazine. Because of its effect on the central nervous system, it has been indicated for use as a tranquilizer and sedative in relieving mental agitation, tension, apprehension, or anxiety, and as an agent to control nausea, vomiting and hiccups. Chlorpromazine also serves to reduce by potentiation, narcotic, sedative, and anesthetic requirements to an animal, thereby lessening any risks which may exist in use of the narcotic, sedative or anesthetic. Chlorpromazine has also been employed in psychiatric medicine for control of symptoms exhibited in neuroses and such psychotic conditions as schizophrenias, manic-depressive states, severe personality disorders, involutional psychoses, degenerative states and senile psychoses. Frequently, central nervous system activity depressants suffer from disadvantages such as unwanted side effects, such as allergic reactions, addiction, and the like. Accordingly, there is a need to provide alternative agents having central nervous system depressant activity.

The amide esters of benzoyl alkanoic acids of the invention, hereafter referred to as the "AP-Compounds", may be represented by the formula

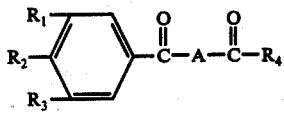

wherein A is alkylene, for instance lower alkylene, e.g., up to about 8 or more carbon atoms, preferably from about 2 up to about 5 carbon atoms, and often is a normal alkylene, e.g., $-(CH_2)_2$, $-(CH_2)_3$, etc.; wherein $R_1$, $R_2$, and $R_3$ may be the same or different and are hydrogen or alkoxy, e.g., lower alkoxy, preferably of up to about 4 carbon atoms such as methoxy; and wherein $R_4$ is heteroacyclic or heterocyclic wherein the hetero atom is nitrogen or oxygen and at least one hetero atom is nitrogen and is bonded to the carbonyl group and is at least secondary, for instance,

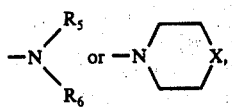

in which $R_5$ and $R_6$ are hydrogen or lower alkyl, preferably of 1 to about 4 carbons, with the proviso that at least one of $R_5$ and $R_6$ is lower alkyl, and $>X$ is oxygen, hydrocarbyl, for instance,

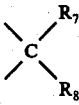

or $>N-R_7$ wherein $R_7$ and $R_8$ may be the same or different and are hydrogen or lower alkyl, preferably of 1 to about 4 carbons.

The AP-Compounds exhibit a central nervous system depressant activity when administered to living animals, e.g., warm-blooded animals such as mammals and humans, for sake of convenience, hereafter referred to by the term "animals". The depressant activity provided by the AP-Compounds resembles the activity exhibited by chlorpromazine. The AP-Compounds may be particularly attractive to provide tranquilizing activity to an animal, that is, to reduce restlessness, agitation, tension, apprehension and anxiety. AP-Compounds may also be employed as a sedative or with a sedative, anesthetic, narcotic or the like to induce sleep, or hypnosis, anesthesia, or the like. Some AP-Compounds may also be used as anticonvulsants, and may be employed to treat mental disorders in which the depressing of the activity of the central nervous system is desired.

Exemplary of the compounds of this invention are

N,N'-diethyl-γ-(3,4,5-trimethoxybenzoyl)-butyramide;
N-morpholinyl-γ-(3,4,5-trimethoxybenzoyl)-butyramide;
N-piperidinyl-γ-(3,4,5-trimethoxybenzoyl)-butyramide;
N-morpholinyl-β-benzoyl-propionamide; N-(4-methyl)-piperazinylγ-(3,4,5-trimethoxybenzoyl)-butyramide hydrochloride;
N-morpholinyl-β-(4-methoxybenzoyl)-propionamide;
N-morpholinyl-γ-(4-methoxybenzoyl)-butyramide;
and N-morpholinyl-γ-benzoylbutyramide.

The AP-Compounds may be prepared from a benzoyl alkanoic acid or acid halide, for instance, chloride, and an amine. Benzoyl alkanoic acids and acid halides of the formula

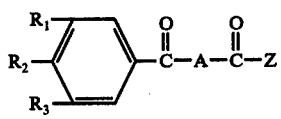

wherein A, $R_1$, $R_2$, and $R_3$ are as defined above and Z is —OH or halogen, for instance, chlorine, are known. U.S. Pat. No. 3,803,222, issued Apr. 4, 1974, to Aldo Garzia discloses the preparation of benzoyl alkanoic acids, and is hereby incorporated by reference. The benzoyl alkanoic acids, for instance, 3,4,5-trimethoxybenzoyl-butyric acid may be prepared by the reaction of a corresponding alkyl benzoylacetate with alkyl β-bromopropionate in the presence of sodium at low temperature, e.g., 0° C., followed by hydrolysis of the crude ester with sulfuric acid. The acid halide may be prepared for the corresponding acid by conventional procedures, for instance, by reaction with thionyl chloride, oxalyl chloride, or the like. The amine reactant may be represented by the formula $H-R_4$ wherein $R_4$ is defined above. Amines which may be employed to provide the compounds of the invention include diethylamine, morpholine, piperidine, 4-methylpiperazine, and the like.

When proceeding with the benzoyl alkanoic acid route of synthesizing the AP-Compounds, which is the preferred route of synthesis, the benzoyl alkanoic acid may be converted to an acid anhydride as an intermediate, then reacted with the amine to provide the AP-Compound. The acid anhydride may be prepared by reacting the benzoyl alkanoic acid with an alkyl ester of a haloformate (i.e., halocarbonate), particularly a chloroformate. The alkyl ester may be a lower alkyl ester, and ethyl chloroformate and isobutyl chloroformate are preferred. The reaction proceeds at room temperature; however, higher or lower reaction temperatures may be employed. The reaction temperature should not be so low to unduly slow the reaction rate or so high as to lead to the deterioration of the starting materials or products. Often a temperature of about 0° to 50° C. or more may be used. The reaction produces a hydrogen halide by-product. A hydrogen halide acceptor, such as a tertiary amine may be employed. A preferred hydrogen halide acceptor is triethylamine. Triethylamine hydrochloride, for instance, will precipitate out from a benzene menstruum. The reaction is preferably conducted under essentially anhydrous conditions and in the presence of an inert organic solvent, for instance, benzene, toluene, and the like.

The intermediate compound, or mixed acid anhydride, may be represented by the formula

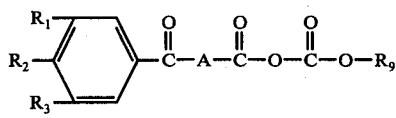

wherein A, $R_1$, $R_2$, and $R_3$ are as defined above and $R_9$ is lower alkyl. The mole ratio of benzoyl alkanoic acid to alkyl haloformate may range widely; although, since the alkyl haloformate may often be more readily obtained, it may be employed in excess of that required for completion of the reaction on a stoichiometric basis. Frequently the mole ratio of benzoyl alkanoic acid to alkyl haloformate may be about 0.1:1 to 5:1, preferably about 0.5:1 to 1.1:1. The hydrogen halide acceptor may also be employed in widely varying amounts, preferably in a mole ratio to the benzoyl alkanoic acid of about 0.1:1 to 10:1, more preferably about 0.8:1 to 1.5:1. The solvent may be provided in solvent-providing quantities, for instance, about 5 to 1000 milliliters per gram of benzoyl alkanoic acid.

It is generally preferable to add the amine to the reaction mixture subsequent to the addition of the alkyl haloformate. The reaction between the amine and the mixed acid anhydride proceeds at room temperature, although higher and lower temperatures may be employed under the same constraints as those for the preparation of the mixed acid anhydride. Often, a temperature of about 0° to 50° C. or more is employed. Since the amine may often be more readily available than the mixed acid anhydride, it is preferably employed in excess of that required for reaction on a stoichiometric basis with the benzoyl alkanoic acid. Frequently, in the mole ratio of benzoyl alkanoic acid to amine may be about 0.5:1 to 20:1, preferably about 1.5:1 to 3:1. The reaction proceeds quickly, particularly under agitation, and the reaction may be substantially complete in about 0.01 to 50 hours at room temperature.

The amide ester of benzoyl alkanoic acid may be recovered by conventional means, for instance, by filtering out the hydrogen halide acceptor; washing the organic phase; neutralizing, if desired, with, for instance, sodium bicarbonate; concentrating, e.g., by evaporation; and separating, and then recrystallizing the product from solvent.

In the process of preparing the AP-Compounds in which the acid halide is employed as a starting material, the reaction with the amine may be conducted in the presence of a base, for instance, an alkali metal base, such as sodium hydroxide or potassium hydroxide, or pyridine, at ambient temperatures. Temperatures of about 0° to 100° C. may be used. The base serves as a halide acceptor. The mole ratio of acid halide to amine may be in the range of about 0.1:1 to 10:1 and the mole ratio of acid halide to base may be in the range of about 0.1:1 to 10:1. The reaction may be conducted in an inert solvent such as benzene, toluene and the like.

In the method for depressing activity of the central nervous system in accordance with the invention, the dosage of AP-Compounds, which can be administered, can vary widely within rather broad limits to provide the desired central nervous system depressant activity effect. The dosages generally range from at least about 1 mg./kg./day (milligrams per kilograms of body weight per day), preferably about 1 to 1000 mg./kg./day, and more preferably about 2 to 200 or 500 mg./kg./day. A dosage may comprise one AP-Compound or two or more AP-Compounds in their mixture.

The AP-Compounds may be administered, for therapeutical purposes, to a host in any convenient manner; however, internal administration is preferred. The administration, for example, may be oral, or parenteral, e.g., by cutaneous, subcutaneous, percutaneous, intraarterial, intraperitoneal, intravenous, intramuscular, and the like, injections. The AP-Compounds are generally more effective when administered parenterally than orally, and thus smaller doses can be administered to achieve a given result. Oral administration may, however, be more convenient and more acceptable to the host. The AP-Compounds may be administered once a day, or fractionally at periodic intervals throughout the day. When orally administered, two or three or more fractional doses per day are preferred. Unit dosage forms, containing about 50 to 500 milligrams of the compound are quite satisfactory and may be prepared according to techniques known to those skilled in the art.

In connection with oral administration, the AP-Compounds may be compounded in a pharmaceutical dosage form such as a pill, lozenge, tablet or capsule, in a pharmaceutically-acceptable carrier. These unit dosage forms may contain the normal diluents, excepients, lubricating agents, and extenders regularly employed in compounding such forms. Exemplary carriers are solids such as lactose, magnesium stearate, calcium sterate, starch, terra alba, dicalcium phosphate, sucrose, talc, stearic acid, gelatin, agar, pectin or acacia.

Alternatively, the AP-Compounds may be suspended in or dissolved in a liquid vehicle suitable for oral administration. The final preparation may be in the form of a solution, emulsion, suspension, syrup or the like. Liquid carriers which may be employed include, for instance, peanut oil, sesame oil, olive oil, water, and the like. The liquid preparation may also contain wetting agents and other conventional additives for liquid pharmaceutical dosage forms.

The AP-Compounds may also be contained in a suitable sterile solution or suspension in a pharmaceutically-acceptable carrier for parenteral injections. AP-Compounds having tertiary amine groups, such as N-(4-methyl)-piperazinyl-γ-(3,4,5-trimethoxybenzoyl)-butyramide, may be provided in the form of their hydrochloride salt and may be soluble in water which may be desirable for parenteral administration.

In addition, the AP-Compounds used in the method of the invention, or compositions containing the same, may be either administered together with or include other physiologically-active materials and/or medicaments, e.g., buffering agents, antacids, sedatives, tranquilizers, analgesics, anasthetics, or the like. It will be understood that the compositions employed in the method of this invention can be brought into a unit dosage form by any suitable technique known to one skilled in the art.

The preparation of AP-Compounds is illustrated in the following examples. All parts and percentages are by weight and the procedures are conducted at ambient conditions unless otherwise indicated.

EXAMPLE 1

A suspension of 14 grams (0.05 mole) of 3,4,5-trimethoxybenzoyl-γ-butyric acid (J. Am. Chem. Soc., 75, 720, 1955) in 400 milliliters of dry benzene is prepared and 5.25 grams of triethylamine are added thereto. To the suspension at room temperature is added 7.5 grams of ethyl chloroformate, thereby providing the mixed acid anhydride. When the addition of the ethyl chloroformate is complete, 9 grams (0.1 mole) of morpholine is added and the mixture is stirred for two hours, then filtered to remove precipitated triethylamine hydrochloride. The mother liquor is washed with an aqueous sodium bicarbonate solution and then concentrated by evaporation to a small volume to provide a solid product and sufficient liquid for filtration, e.g., about 20 to 40 milliliters. Solid product which is obtained, is crystallized from methanol to provide about 13 grams of N-morpholinyl- γ-(3,4,5-trimethoxybenzoyl)-butryamide having a melting point of 105° to 107° C.

EXAMPLE 2

A suspension of 17.8 grams (0.1 mole) of β-benzoyl-propionic acid (Organic Synthesis, 2, 81) in 500 milliliters of dry benzene is prepared and 10.5 grams of triethylamine, 15 grams of ethyl chloroformate, and 18 grams (0.2 mole) of morpholine are sequentially added. The suspension is stirred for two hours at room temperature and then filtered to remove the precipitated triethylamine hydrochloride. The mother liquor is evaporated to a small amount for filtration and the solid product which is obtained, is separated by filtration and crystallized from ethanol to provide about 15 grams of N-morpholinyl-β-benzoyl-propionamide having a melting point of 87°-89° C.

EXAMPLE 3

A suspension of 14 grams (0.05 mole) of 3,4,5-trimethoxybenzoyl-γ-butyric acid in 400 milliliters of dry benzene is prepared, and 5.25 grams of triethylamine, 7.5 grams of ethyl chloroformate, and then 7.5 grams (0.1 mole) of diethylamine are added thereto. The suspension is stirred for two hours at room temperature and then filtered to remove the precipitated triethylamine hydrochloride. The mother liquor is evaporated until a dry product, i.e., a residual oil, is obtained. The residual oil becomes solid after treatment with diethyl ether and is then filtered to provide 10 grams of N,N'-diethyl-γ-(3,4,5-trimethoxybenzoyl)-butyramide.

EXAMPLE 4

The procedure of example 1 is essentially repeated except that piperidine is used instead of morpholine. The product is N-piperidinyl-γ-(3,4,5-trimethoxybenzoyl)-butyramide having a melting point of 65° to 68° C.

EXAMPLE 5

The procedure of example 1 is essentially repeated except that 4-methyl piperazine is used instead of morpholine. The product is N-(4-methyl)-piperazinyl-γ-(3,4,5-trimethoxybenzoyl)-butyramide hydrochloride having a melting point of 104°-106° C.

EXAMPLE 6

The procedure of example 1 is essentially repeated except that 4-methoxybenzoyl-β-propionic acid is used instead of 3,4,5-trimethoxybenzoyl-γ-butyric acid. The product is N-morpholinyl-β-(4-methoxybenzoyl)-propionamide having a melting point of 85° to 87° C.

EXAMPLE 7

The procedure of example 1 is essentially repeated except that 4-methoxybenzoyl-γ-butyric acid is used instead of 3,4,5-trimethoxybenzoyl-γ-butyric acid. The product is N-morpholinyl-γ-(4-methoxybenzoyl) butyramide having a melting point of 92° to 93° C.

EXAMPLE 8

The procedure of example 1 is essentially repeated except that γ-benzoyl-butyric acid is employed instead of γ-(3,4,5-trimethoxybenzoyl)-butyric acid. The product is N-morpholinyl-γ-benzoyl-butyramide having a melting point of 59° to 61° C.

A clinically-useful substance for depressing the activity of the central nervous system may affect the spontaneous motility of an animal when administered thereto. The administration of chlorpromazine to a mouse, for instance, provides a reduction in the spontaneous movement of the animal, and the animal appears quieter and less restless. In the following example, AP-Compounds are administered to mice and the spontaneous motility of the mice is observed. In each instance, the AP-Compounds provide a reduction in the spontaneous movement of the animals, thereby indicating the existance of a depressing activity on the central nervous system and a tranquilizing effect.

EXAMPLE 9

AP-Compounds are intraperitoneally administered to adult mice which are then observed for spontaneous motility. Spontaneous motility is measured by placing the mice in a cage having a light beam passing therethrough. Interruptions of the light beam caused by movement of the mice are recorded. The relative number of interruptions after treatment of the mice as compared to before treatment is an indication of the reduction in spontaneous motility caused by the activity of the AP-Compound. Since the mice may be subjected to a shock due to the intraperitoneal administration of any substance, a control is conducted in which the mice are intraperitoneally-administered a saline solution. The results are provided in Table I, and for sake of comparison, the spontaneous motility is expressed as a percent value of the spontaneous motility before treatment.

TABLE I

| Run No. | Substance Administered | Dosage mg./kg. | Spontaneous Motility as a Percent Value of Spontaneous Motility before Treatment |
|---|---|---|---|
| 1 | AP-Compound of Ex. 1 | 200 | 21 |
|   | Control | — | 74 |
| 2 | AP-Compound of Ex. 1 | 50 | 34 |
|   | Control | — | 77 |
| 3 | AP-Compound of Ex. 1 | 25 | 44 |
|   | Control | — | 78 |
| 4 | AP-Compound of Ex. 1 | 25 | 29 |
|   | Control | — | 80 |
| 5 | AP-Compound of Ex. 1 | 10 | 29 |
|   | Control | — | 75 |
| 6 | AP-Compound of Ex. 2 | 100 | 16 |
|   | Control | — | 74 |
| 7 | AP-Compound of Ex. 2 | 25 | 16 |
|   | Control | — | 77 |
| 8 | AP-Compound of Ex. 2 | 10 | 35 |
|   | Control | — | 78 |
| 9 | AP-Compound of Ex. 2 | 10 | 26 |
|   | Control | — | 80 |
| 10 | AP-Compound of Ex. 2 | 5 | 65 |
|   | Control | — | 75 |
| 11 | AP-Compound of Ex. 7 | 10 | 33 |
|   | AP-Compound of Ex. 7 | 5 | 41 |
|   | Control | — | 70 |
| 12 | AP-Compound of Ex. 8 | 10 | 28 |
|   | Control | — | 87 |
| 13 | AP-Compound of Ex. 8 | 10 | 30 |
|   | Control | — | 75 |

In addition to the data provided in Table I, it may be noted that the AP-Compound of example 6 exhibits less activity in depressing the spontaneous motility of mice than the AP-Compound of example 1. The comparison, chlorpromazine, on a weight basis, exhibits slightly more activity in depressing the spontaneous motility of mice than the AP-Compound of example 1.

Another indication of the effect of the AP-Compounds on the activity of the central nervous system is the well-known test for suppression of the conditioned avoidance response of animals. One mode of this test is to condition, for instance, rats to move to an unelectrified compartment of a test cage when acoustic and visual warning signals are given. The relative time after the signals for the previously conditioned subject to enter the unelectrified compartment of the test cage after administration of a substance as compared to before is an indication of the suppression, or enhancement, of a conditioned avoidance response.

EXAMPLE 10

A conditioning cage having two chambers with free access between chambers is used to observe conditioned avoidance response in rats. The floor of one of the compartments is adapted to be electrically activated to deliver a mild shock to the rat. The rats are conditioned by first giving acoustic and visual warning signals to the rat, and then, after a short period of time, activating the floor to deliver an electrical shock to any rat which has not entered the unelectrified compartment. Eventually, the rats learn to leave the electrified compartment after the warning signal and thus are conditioned.

Various amounts of the AP-Compounds of examples 1 and 2 are administered intraperitoneally to conditioned rats. As in Example 9, a saline solution is administered to rats used in control groups. The results are provided in Table II and illustrate the mean waiting time for the conditioned response in 1/12 second time units.

TABLE II

| Run No. | Substance Administered | Dosage (mg/kg.) | No. of Animals | Mean Total Waiting Time Days before Treatment 2 | Mean Total Waiting Time Days before Treatment 1 | Day of Treatment |
|---|---|---|---|---|---|---|
| 1 | AP-Compound of Example 1 | 50 | 4 | 895 | 837 | 914 |
|   | AP-Compound of Example 1 | 100 | 3 | 1009 | 946 | 1270 |
|   | AP-Compound of Example 1 | 150 | 3 | 881 | 826 | 1200 |
|   | Control | — | 4 | 835 | 789 | 684 |
| 2 | AP-Compound of Example 2 | 50 | 4 | — | 986 | 1008 |
|   | AP-Compound of Example 2 | 100 | 4 | — | 934 | 1480 |
|   | Control | — | 4 | — | 957 | 909 |
| 3 | Chlorpromazine | 5 | 4 | — | 872 | 1269 |
|   | Chlorpromazine | 2.5 | 4 | — | 960 | 1214 |
|   | Control | — | 4 | — | 1026 | 880 |

As illustrated in Table II, the AP-Compounds provide a depressing activity on the central nervous system. The activity, e.g., with AP-Compounds wherein A is alkylene of about 2 or 3 carbons and $R_4$ is morpholinyl, appears to be relatively insignificant at lower dosages, i.e., 50 mg./kg., of N-morpholinyl-$\gamma$-(3,4,5-trimethoxybenzoyl)-butyramide and N-morpholinyl-$\beta$-benzoyl-propionamide. On the other hand, significant suppression of the conditioned avoidance response is provided by the administration of as little as 2.5 and 5 mg./kg. of chlorpromazine. If a significant suppression of the conditioned avoidance response is desired using the AP-Compounds, such a suppression can be achieved employing greater amounts of the AP-Compounds, for instance, 100 mg./kg.

Another activity which is exhibited by chlorpromazine is the potentiation of barbituate induced sleep, or hypnosis, by the preadministration of chlorpromazine. The following example illustrates the activity of the AP-Compounds on the central nervous system by the potentiation of barbituateinduced hypnosis test.

EXAMPLE 11

The sedative effect of AP-Compounds is observed by administering the compound to a mouse followed by the intraperitoneal administration of 15 milligrams of sodium pentobarbital per kilogram of weight of the mouse. The period of hypnosis is herein defined as that period of time which the animals lose their righting reflexes. In the control runs, only the sodium pentobarbital is administered to the mice in the control group. The results are provided in Table III.

TABLE III

| Substance Administered | Dosage (mg/kg) | Mode of Administration | No. of Animals | No. of Animals under Hypnosis | Mean Period of Hypnosis, Minutes | No. of Animals Which Died |
|---|---|---|---|---|---|---|
| AP-Compound o | 250 | i.p. | 4 | 4 | >159 | 2 |

TABLE III-continued

| Substance Administered | Dosage (mg/kg) | Mode of Administration | No. of Animals | No. of Animals under Hypnosis | Mean Period of Hypnosis, Minutes | No. of Animals Which Died |
|---|---|---|---|---|---|---|
| AP-Compound of Example 1 | 125 | i.p. | 4 | 4 | 120 | 0 |
| AP-Compound of Example 1 | 50 | i.p. | 4 | 4 | 52 | 0 |
| Control | — | — | 10 | 2 | 1-2 | 0 |
| AP-Compound of Example 1 | 250 | oral | 4 | 4 | 106 | 0 |
| AP-Compound of Example 1 | 125 | oral | 4 | 2 | 51-52 | 0 |
| Control | — | — | 4 | 0 | 0 | 0 |
| AP-Compound of Example 2 | 25 | i.p. | 4 | 3 | 6 | 0 |
| AP-Compound of Example 2 | 50 | i.p. | 4 | 4 | 38 | 0 |
| AP-Compound of Example 2 | 100 | i.p. | 4 | 4 | 88 | 0 |
| Control | — | — | 8 | 0 | 0 | 0 |

When, for instance, chlorpromazine is intraperitoneally administered to rats in dosages of 25 and 12.5 mg./kg. weight, followed by the intraperitoneal administration of 15 mg./kg. of sodium pentobarbital, the mean hypnosis period is 165 and 137 minutes, respectively. Four rats are employed as the test group for each dosage level. One death occurs in each of the groups.

In another test, N-morpholinyl-γ-(3,4,5-methoxybenzoyl)-butyramide is intraperitoneally administered to mice which have previously been trained to stand on a rotating bar for three minutes. At a dosage of 250 mg./kg., none of five mice tested is able to stand on the rotating bar for the three minute period; however, at a dosage of 125 mg./kg., two out of five mice tested are able to complete the task.

The anticonvulsant effect of N-morpholinyl-β-benzoyl-propionamide and N-morpholinyl- γ-(4-methoxybenzoyl)butyramide, which are AP-Compounds in which at least one of $R_1$, $R_2$ and $R_3$ is hydrogen and $R_4$ is morpholinyl, is determined by subjecting treated mice to electroshock. The electroshock is administered through ear electrodes. A typical procedure is through the use of stimulation parameters which may induce the maximum electroshock seizure (MES). This may be obtained by applying rectangular input shocks for 0.6 second. Each input may last 0.4 millisecond and the input frequency may be about 25 hertz. A dosage of about 25 mg./kg. of N-morpholinylβ-benzoyl-propionamide protects the mouse from electroshock and the latter AP-Compounds also exhibits a clear anticonvulsant effect, but the effect is not as marked. N-morpholinyl-γ-(3,4,5-trimethoxybenzoyl)-butyramide does not antagonize the convulsant effect of strychnine or electroshock in a rat even at dosages as high as 250 mg./kg., intraperitoneally administered.

EXAMPLE 12

Various Ap-Compounds are intraperitoneally administered to mice and the behavior of the mice is observed. The results are provided in Table IV.

TABLE IV

| Substance Administered | Dosage, mg/kg | Remarks |
|---|---|---|
| AP-Compound of Example 1 | 100 | Weak sedation |
| AP-Compound of Example 1 | 200 | Sedation |
| AP-Compound of Example 1 | 300 | Sedation |
| AP-Compound of Example 1 | 50 | Weak sedation |
| AP-Compound of Example 1 | 25 | Mild excitement, no sedation |
| AP-Compound of Example 6 | 100 | No effect |
| AP-Compound of Example 6 | 200 | Weak sedation |
| AP-Compound of Example 6 | 300 | Marked sedation |
| AP-Compound of Example 2 | 100 | Sedation |
| AP-Compound of Example 2 | 200 | Sleeping for 20 min. |
| AP-Compound of Example 2 | 300 | Sleeping for 30 min. |
| AP-Compound of Example 2 | 25 | Sedation |
| AP-Compound of Example 2 | 12.5 | Mild excitement followed by sedation |

The toxicity and effect on boy temperature and blood pressure provided by the AP-Compounds are also investigated.

EXAMPLE 13

The AP-Compound of example 1 is administered to adult Wistar rats and adult Swiss rats to determine acute toxicity. The results employing the Wistar rats is provided in Table V and Swiss rats, in Table VI.

TABLE V

| Mode of Administration | Dosage (mg/kg) | Died/Treated | Sedated/Treated | Sleeping/Treated |
|---|---|---|---|---|
| i.p. | 50 | 0/4 | 0/4 | 0/4 |
| i.p. | 100 | 0/4 | 0/4 | 0/4 |
| i.p. | 150 | 0/4 | 4/4 S.L. | 0/4 |
| i.p. | 200 | 0/4 | 4/4 | 0/4 |
| i.p. | 250 | 0/4 | 4/4 | 0/4 |
| i.p. | 500 | 0/4 | 4/4 S.I. | 0/4 |
| i.p. | 750 | 1/4 | 4/4 | 4/4 |
| i.p. | 1,000 | 4/4 | 4/4 | 4/4 |
| oral | 250 | 0/4 | 0/4 | 0/4 |
| oral | 500 | 0/4 | 4/4 | 0/4 |
| oral | 1,000 | 0/4 | 4/4 S.I. | 0/4 |

S.L. = Weak sedation
S.I. = Marked sedation

TABLE VI

| Mode of Administration | Dosage (mg/kg) | Sedated/Treated | Died/Treated |
|---|---|---|---|
| i.p. | 1,000 | 4/4 | 0/4 |
| i.p. | 1,200 | 4/4 | 2/4 |
| i.p. | 1,400 | 4/4 | 3/4 |
| i.p. | 1,600 | 4/4 | 4/4 |
| i.p. | 1,800 | 4/4 | 4/4 |
| oral | 1,000 | 4/4 | 0/4 |
| oral | 1,400 | 4/4 | 0/4 |
| oral | 1,600 | 4/4 | 0/4 |
| oral | 2,000 | 4/4 | 0/4 |

EXAMPLE 14

The AP-Compound of example 1 is administered to rats and the effect of the AP-Compound on the mean rectal temperature is observed. The results are provided in Table VII.

TABLE VII

| Run No. | Substance Administered | No. of Animals | Mode of Administration | Dosage (mg/kg) | Mean Rectal Temperature in ° C | | | | |
|---|---|---|---|---|---|---|---|---|---|
| | | | | | 0' | 30' | 60' | 90' | 120' |
| 1 | Vehicle | 5 | i.p. | — | 37.8 ± 1.2 | 37.7 ± 0.5 | 37.7 ± 0.7 | 37.5 ± 0.5 | 37.5 ± 0.5 |
| | AP-Compound | 5 | i.p. | 200 | 37.5 ± 0.7 | 34.2 ± 0.5 | 33.4 ± 0.6 | — | 33.4 ± 0 |
| 2 | Vehicle | 5 | oral | — | 37.8 ± 0.8 | 37.7 ± 0.7 | 37.6 ± 0.3 | 37.5 ± 0.7 | 37.5 ± 0.5 |
| | AP-Compound | 5 | oral | 500 | 37.7 ± 0.8 | 37.1 ± 0.0 | 36.4 ± 0.4 | 36.2 ± 0.0 | 35.8 ± 0.8 |
| | AP-Compound | 5 | oral | 400 | 37.7 ± 0.7 | 37.4 ± 0.8 | 36.9 ± 0.4 | 36.8 ± 0.4 | 36.6 ± 0.0 |
| | AP-Compound | 5 | oral | 200 | 37.7 ± 0.0 | 37.4 ± 0.3 | 37.3 ± 0.5 | 37.4 ± 0.0 | 37.3 ± 0.3 |

Also, the effect of administration of N-morpholinyl-γ-(3,4,5-trimethoxybenzoyl)-butyramide on the blood pressure is observed. The effect observed is mild and consists of a blood pressure reduction only when high doses are administered, which may sometimes be preceded by a modest rise in blood pressure. This is the type of effect which is observed with other central nervous system activity depressant substances.

It is claimed:

1. A compound of the formula

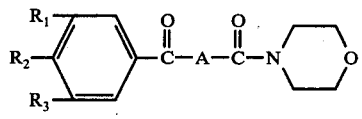

wherein A is lower alkylene and $R_1$, $R_2$ and $R_3$ are lower alkoxy.

2. A compound of the formula

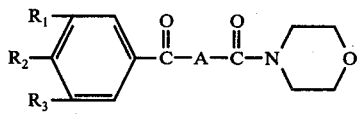

wherein A is —$(CH_2)_3$— and $R_1$, $R_2$ and $R_3$ are methoxy.

3. A pharmaceutical composition for treatment of a host in need of depressing the activity of the central nervous system or tranquilizing comprising a pharmaceutically-acceptable carrier and as the active ingredient in an amount sufficient to provide the depressant or tranquilizing activity a compound of the formula:

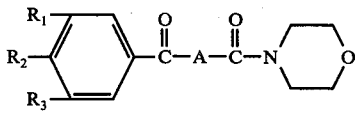

wherein A is lower alkylene and each of $R_j$, $R_2$ and $R_3$ is hydrogen or lower alkoxy with the proviso that the compound is other than N-morpholinyl-β-benzoylpropionamide.

4. A pharmaceutical composition for treatment of a host in need of depressing the activity of the central nervous system comprising a pharmaceutically-acceptable carrier and as the active ingredient in an amount sufficient to provide the depressant activity a compound of the formula:

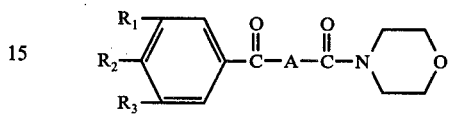

wherein A is —$(CH_2)_3$— and $R_1$, $R_2$ and $R_3$ are methoxy, A is —$(CH_2)_3$— and $R_1$ and $R_3$ are hydrogen and $R_2$ is methoxy, A is —$(CH_2)_2$— and $R_1$ and $R_3$ are hydrogen and $R_2$ is methoxy, or A is —$(CH_2)_3$— and $R_1$, $R_2$ and $R_3$ are hydrogen.

5. A pharmaceutical composition for treatment of a host in need of depressing the activity of the central nervous system or tranquilizing comprising a pharmaceutically-acceptable carrier and as the active ingredient in an amount sufficient to provide the depressant or transquilizing activity a compound of the formula:

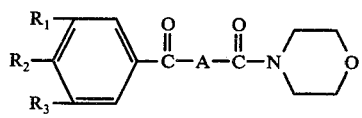

wherein A is lower alkylene and each of $R_1$, $R_2$ and $R_3$ is hydrogen or lower alkoxy with the proviso that at least one of $R_1$, $R_2$ and $R_3$ is lower alkoxy.

6. A method for providing central nervous system depressant activity to a host comprising administering to the host an effective amount to provide the depressant activity of a compound of the formula

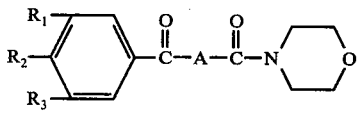

wherein A is lower alkylene and each of $R_1$, $R_2$ and $R_3$ is hydrogen or lower alkoxy.

7. A method for providing tranquilizing activity to a host comprising administering to the host an effective amount to provide the tranquilizing activity of a compound of the formula

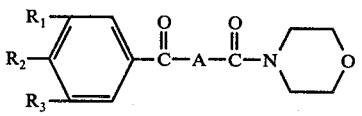

wherein A is lower alkylene and each of $R_1$, $R_2$ and $R_3$ is hydrogen or lower alkoxy.

8. A method for providing sedative activity to a host comprising administering to the host an effective amount to provide the sedative activity of a compound of the formula

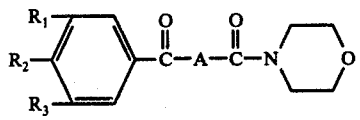

wherein A is lower alkylene and each of $R_1$, $R_2$ and $R_3$ is hydrogen or lower alkoxy.

9. A method of claim 7 in which A is normal alkylene.

10. A method of claim 7 in which A contains about 2 to 5 carbon atoms.

11. A method of claim 7 in which the compound is N-morpholinyl-γ-(3,4,5-trimethoxybenzoyl)-butyramide,
N-morpholinyl-β-benzoyl-propionamide,
N-morpholinyl-β-(4-methoxybenzoyl)-propionamide,
N-morpholinyl-γ-(4-methoxybenzoyl)-butyramide; or
N-morpholinyl-γ-benzoyl-butyramide.

12. The method of claim 11 wherein the host is a warm-blooded mammal.

13. A method for providing anticonvulsant activity to a host comprising administering to the host an effective amount to provide the anticonvulsant activity of N-morpholinyl-β-benzoyl-propionamide or N-morpholinyl-γ-(4-methoxybenzoyl)-butyramide.